(12) United States Patent
Sawant et al.

(10) Patent No.: US 8,097,729 B2
(45) Date of Patent: Jan. 17, 2012

(54) POLYMORPHIC FORM OF LERCANIDIPINE HYDROCHLORIDE AND PROCESS FOR THE PREPARATION THEREOF

(75) Inventors: Mangesh Shivram Sawant, Mumbai (IN); Maloyesh Mathuresh Biswas, Maharashtra (IN); Mubeen Ahmed Khan, Maharastra (IN); Sukumar Sinha, Maharastra (IN); Nitin Sharad Chandra Pradhan, Thane (IN)

(73) Assignee: Glenmark Generics Ltd., Mumbai (IN)

( * ) Notice: Subject to any disclaimer, the term of this patent is extended or adjusted under 35 U.S.C. 154(b) by 477 days.

(21) Appl. No.: 11/992,181

(22) PCT Filed: Sep. 18, 2006

(86) PCT No.: PCT/IB2006/002579
§ 371 (c)(1),
(2), (4) Date: Feb. 27, 2009

(87) PCT Pub. No.: WO2007/031865
PCT Pub. Date: Mar. 22, 2007

(65) Prior Publication Data
US 2009/0221833 A1 Sep. 3, 2009

Related U.S. Application Data

(60) Provisional application No. 60/751,834, filed on Dec. 20, 2005.

(30) Foreign Application Priority Data

Sep. 16, 2005 (IN) .......................... 1125/MUM/2005
Jan. 17, 2006 (IN) ............................. 75/MUM/2006
Mar. 24, 2006 (IN) ........................... 437/MUM/2006

(51) Int. Cl.
*C07D 213/80* (2006.01)
*A61K 31/44* (2006.01)

(52) U.S. Cl. ........................................ 546/321; 514/356

(58) Field of Classification Search ........................ None
See application file for complete search history.

(56) References Cited

U.S. PATENT DOCUMENTS

| | | | |
|---|---|---|---|
| 5,912,351 | A | 6/1999 | Leonardi et al. |
| 6,852,737 | B2 | 2/2005 | Bonifacio et al. |

FOREIGN PATENT DOCUMENTS

| | | |
|---|---|---|
| EP | 0 153 016 | 8/1985 |
| EP | 1 423 367 | 4/2005 |
| WO | WO 96/35668 | 11/1996 |
| WO | WO 03/014084 | 2/2003 |
| WO | WO 2006/059332 | 6/2006 |
| WO | WO 2006/134606 | 12/2006 |

OTHER PUBLICATIONS

Leonardi et al., "Asymmetric N-(3,3-diphenylpropyl)aminoalkyl esters of 4-aryl-2,6-dimethyl-1,4-diliydropyridine-3,5-dicarboxylic acids with antihypertensive activity", *Eur. J. Med. Chem.*, vol. 33 (1998) 399-420.

*Primary Examiner* — Janet Andres
*Assistant Examiner* — Heidi Reese
(74) *Attorney, Agent, or Firm* — M. Carmen & Associates, PLLC (57) ABSTRACT

Processes for the purification of lercanidipine hydrochloride are provided which uses a binary system of an alcohol-containing solvent such as methanol and an aliphatic ester-containing solvent such as isopropyl acetate. Processes for the preparation of substantially amorphous lercanidipine hydrochloride are also provided. Also provided is lercanidipine hydrochloride substantially in polymorph form V.

16 Claims, 3 Drawing Sheets

POLYMORPHIC FORM OF LERCANIDIPINE HYDROCHLORIDE AND PROCESS FOR THE PREPARATION THEREOF

PRIORITY

This application claims [the benefit under 35 U.S.C. §119] priority under 35 U.S.C. §371 to International Application No. PCT/IB2006/002579, filed Sep. 18, 2006 and entitled "POLYMORPHIC FORM OF LERCANIDIPINE HYDROCHLORIDE AND PROCESS FOR THE PREPARATION THEREOF", which claims priority to Indian Provisional Application No. 437/MUM/2006, filed on Mar. 24, 2006, and entitled "SUBSTANTIALLY PURE LERCANIDIPINE HYDROCHLORIDE AND PROCESS FOR THE PREPARATION THEREOF" and to Indian Provisional Application No. 75/MUM/2006, filed on Jan. 17, 2006, and entitled "POLYMORPHIC FORM V OF LERCANIDIPINE HYDROCHLORIDE AND PROCESS FOR THE PREPARATION THEREOF" and to U.S. Provisional Application No. 60/751,834, filed on Dec. 20, 2005, and entitled "POLYMORPHIC FORM V OF LERCANIDIPINE HYDROCHLORIDE AND PROCESS FOR THE PREPARATION THEREOF", and to Indian Provisional Application No. 1125/MUM/2005, filed on Sep. 16, 2005, and entitled "NOVEL POLYMORPHIC FORMS OF LERCANIDIPINE HYDROCHLORIDE AND PROCESS FOR ITS PREPARATION", the contents of each of which are incorporated by reference herein.

BACKGROUND OF THE INVENTION

1. Technical Field

The present invention generally relates to a novel polymorph of lercanidipine hydrochloride and processes for its preparation. The present invention also generally relates to a process for the preparation of an amorphous form of lercanidipine hydrochloride and a process for the purification of lercanidipine hydrochloride.

2. Description of Related Art

Lercanidipine hydrochloride, also known as 1,4-dihydro-2,6-dimethyl-4-(3-nitrophenyl)-3,5-pyridinedicarboxylic acid 2-[(3,3-diphenylpropyl)methylamino]-1,1-dimethylethylmethyl ester hydrochloride, is represented by the structure of Formula I.

(I)

Lercanidipine hydrochloride is a synthetic antihypertensive calcium channel blocker sold under the brand names Lercadip, Lerdip, Lerzam, Zanedip, and Zanidip®. Lercanidipine hydrochloride is a dihydropyridine calcium channel blocker used for the treatment of hypertension. It can reduce systemic arterial blood pressure with a long duration of action and is believed to slow the progression of atherosclerosis. See, e.g., The Merck Index, Thirteenth Edition, 2001, p. 973, monograph 5465.

European Patent No. 0153016 ("the '016 patent") and U.S. Pat. No. 4,968,832 ("the '832 patent"), herein incorporated by reference, disclose lercanidipine hydrochloride. The '016 and '832 patents further disclose processes for the preparation of lercanidipine hydrochloride and the amorphous form of lercanidipine hydrochloride. Drawbacks associated with these processes include, for example, the production of impurities. Accordingly, it would be advantageous to reduce the level of impurities in the preparation of lercanidipine hydrochloride.

U.S. Pat. No. 5,912,351 discloses a simpler process for the preparation of lercanidipine hydrochloride. It involves the reaction of 1,4-dihydro-2,6-dimethyl-5-methoxycarbonyl-4-(3-nitrophenyl)pyridine-3-carboxylic acid with thionyl chloride in dichloromethane and dimethylformamide at a temperature between −4 and +1° C. and subsequent esterification of the obtained acid chloride with 2, N-dimethyl-N-(3,3-diphenylpropyl)-1-amino-2-propyl alcohol at a temperature between −10 and 0° C. The process yields lercanidipine hydrochloride in an anhydrous non-hygroscopic crystalline form, and avoids the formation of unwanted by-products and the subsequent purification on chromatography columns.

One impurity believed to be present in the production of lercanidipine hydrochloride is 1,4-dihydro-2,6-dimethyl-4-(3-nitrophenyl)pyridine-3,5-dicarboxylic acid 2-[N-(3,3-diphenyl propyl)-N-methylamino]-1,1-dimethyl ethyl propyl diester, as determined from an HPLC analysis of different batches of lercanidipine hydrochloride produced by the reaction of butanoic acid, 2-[(3-nitrophenyl)methylene]-3-oxo-2-[(3,3-diphenyl propyl)methylamino]-1,1-dimethyl ethyl ester hydrochloride and methyl-3-amino crotonate in the presence of triethyl amine and in n-propanol employing the procedure set forth in Example 16 of EP 0153016. The structure of 1,4-dihydro-2,6-dimethyl-4-(3-nitrophenyl)pyridine-3,5-dicarboxylic acid 2-[N-(3,3-diphenyl propyl)-N-methylamino]-1,1-dimethyl ethyl propyl diester is represented by the structure of Formula II.

(II)

The impurity is formed due to the transesterification of lercanidipine hydrochloride at the 5 position with n-propanol in the presence of HCl in n-propanol. Additionally, this impurity is highly difficult to remove from crude lercanidipine hydrochloride.

U.S. Pat. No. 6,852,737 ("the '737 patent") discloses crystalline Forms I and II and crude Forms A and B of lercanidipine hydrochloride and processes for their preparation. Crude Form A of lercanidipine hydrochloride is described in Example 2 as having a differential scanning calorimetric (DSC) peak of 150-152° C. Crude Form B of lercanidipine hydrochloride is described in Example 3 as having a DSC peak of 131-135° C. The '737 patent additionally discloses that U.S. Pat. No. 5,912,351 ("the '351 patent") produces a third crude form of lercanidipine hydrochloride, termed crude Form C. Crude Form C is reported to have a DSC peak of 186-192° C. Additionally, the '737 patent discloses that thermogravimetric studies show that crude Form A contains 3-4% residual ethyl acetate, crude Form B contains 0.3-0.7% residual ethyl acetate, and crude Form C contains 0-0.1% residual solvents. Crystalline Forms I and II of lercanidipine hydrochloride are well characterized by XRD analysis in the '737 patent. Example 12 of the '737 patent discloses that crystalline Form I has a melting temperature (T peak) of 198.7° C. and an onset temperature of 179.8° C., and crystalline Form II has a melting temperature (T peak) of 209.3° C. and an onset temperature of 169.0° C.

WO 2006/089787 discloses amorphous lercanidipine hydrochloride having a purity of at least 95% and a method for its preparation. The method includes dissolving crystalline lercanidipine hydrochloride in an organic solvent to provide a solution and isolating amorphous lercanidipine hydrochloride by either (a) adding water to the solution to form a precipitate and collecting the precipitate or (b) evaporating off the organic solvent.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. Additionally, polymorphic forms of the same drug substance or active pharmaceutical ingredient, can be administered by itself or formulated as a drug product (also known as the final or finished dosage form), and are well known in the pharmaceutical art to affect, for example, the solubility, stability, flowability, tractability and compressibility of drug substances and the safety and efficacy of drug products.

The discovery of new polymorphic forms of a pharmaceutically useful compound provides a new opportunity to improve the performance characteristics of a pharmaceutical product. It also adds to the material that a formulation scientist has available for designing, for example, a pharmaceutical dosage form of a drug with a targeted release profile or other desired characteristic. A new polymorphic form of lercanidipine hydrochloride has now been discovered.

Efforts are also made to prepare pharmaceutical products of a high grade and with a minimum amount of impurities present. The control of impurities requires a study of various options to decide upon the reaction conditions and testing protocols necessary to insure that drugs which are administered to the public are substantially pure. Accordingly, there remains a need for an improved process for preparing lercanidipine hydrochloride that eliminates or substantially reduces the impurities in a convenient and cost efficient manner to provide substantially pure forms of lercanidipine hydrochloride.

SUMMARY OF THE INVENTION

In accordance with one embodiment of the present invention, a process for preparing substantially pure lercanidipine hydrochloride is provided comprising (a) dissolving lercanidipine hydrochloride in an alcohol-containing solvent to form a solution, (b) adding an aliphatic ester-containing solvent to the solution; and (c) recovering substantially pure lercanidipine hydrochloride from the solution.

In accordance with a second embodiment of the present invention, a lercanidipine hydrochloride substantially in polymorph form V is provided.

In accordance with a third embodiment of the present invention, a substantially pure lercanidipine hydrochloride in polymorph form V is provided.

Figure 1:
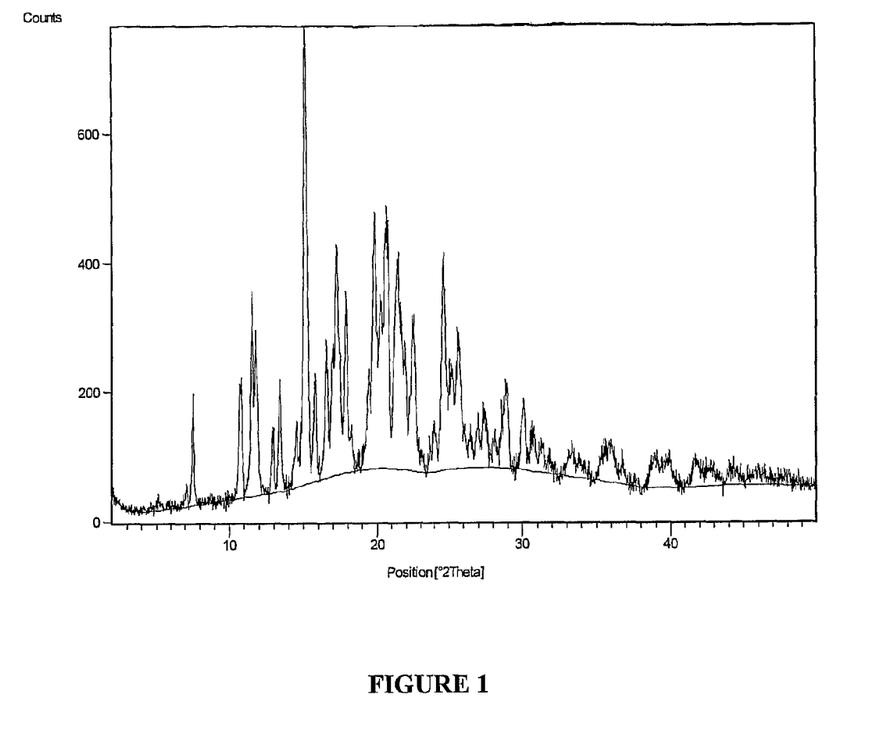
FIG. 1 is a characteristic powder X-ray diffraction (XRD) pattern of polymorph form V of lercanidipine hydrochloride.
Figure 2:
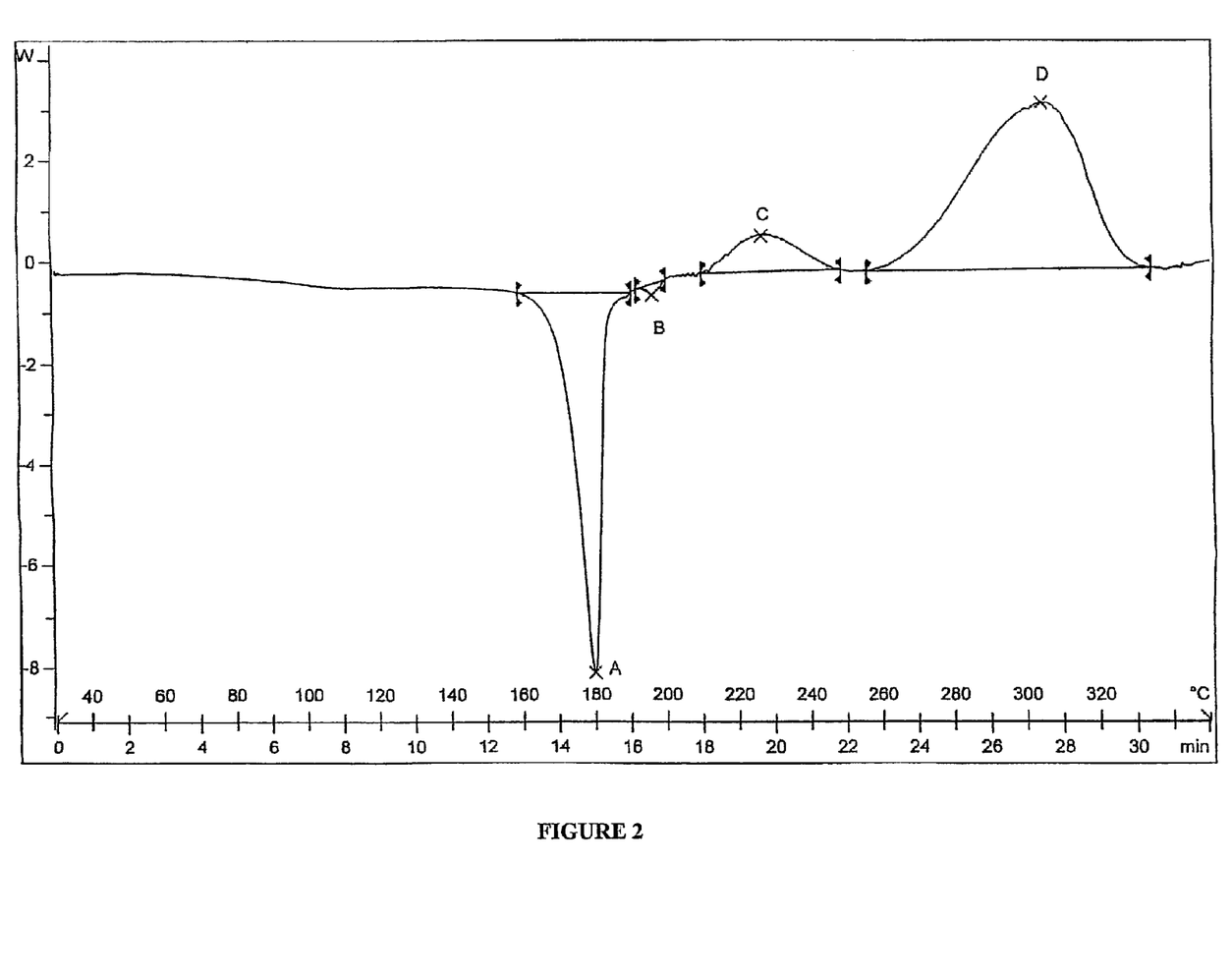
FIG. 2 is a characteristic differential scanning calorimetric (DSC) thermogram of polymorph form V of lercanidipine hydrochloride.

In accordance with a fourth embodiment of the present invention, a lercanidipine hydrochloride substantially in polymorph form V and having at least one of the following characteristics is provided (a) an X-ray diffraction (XRD) pattern substantially in accordance with FIG. 1; and/or (b) a differential scanning calorimetric (DSC) thermogram substantially in accordance with FIG. 2.

In accordance with a fifth embodiment of the present invention, a lercanidipine hydrochloride substantially in polymorph form V is provided and exhibiting characteristic peaks (expressed in degrees 2θ±0.2°θ) at approximately one or more of the positions: about 17.2752 and about 19.8836.

In accordance with a sixth embodiment of the present invention, a process for the preparation of a lercanidipine hydrochloride substantially in polymorph form V is provided, the process comprising:

(a) dissolving lercanidipine hydrochloride in an alcohol-containing solvent to obtain a solution;

(b) adding an aliphatic ester-containing solvent to the solution; and (c) recovering lercanidipine hydrochloride substantially in polymorph form V from the solution.

Advantages of the process of the above mentioned embodiments include at least the following:

1. The process is a relatively simple process which is viable and efficient on a commercial scale and results in a substantially pure lercanidipine hydrochloride.

2. The process provides for improved efficiency because it utilizes inexpensive reagents and produces less waste and fewer impurities.

In accordance with another embodiment of the present invention, a process for preparing an amorphous form of lercanidipine hydrochloride is provided, the process comprising (a) dissolving lercanidipine hydrochloride substantially in polymorph form V in an organic solvent; and (b) recovering the amorphous form of lercanidipine hydrochloride.

In accordance with yet another embodiment of the present invention, a process for preparing an amorphous form of lercanidipine hydrochloride is provided, the process comprising (a) dissolving substantially pure lercanidipine hydrochloride in an organic solvent; (b) treating the solution with a clarifying agent to form a clarified solution, and (c) recovering the amorphous form of lercanidipine hydrochloride.

Advantages of the process of this embodiment include at least the following:

1. The process is a relatively simple process which is viable and efficient on a commercial scale and results in a substantially pure amorphous form of lercanidipine hydrochloride.

2. The process provides for improved efficiency because it utilizes inexpensive reagents and produces less waste and fewer impurities.

DEFINITIONS

The term "treating" or "treatment" of a state, disorder or condition as used herein means: (1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a subject to be treated is either statistically significant or at least perceptible to the patient or to the physician.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host means causing a therapeutically effective blood concentration of the active ingredient at the particular location. This can be accomplished, e.g., by topical, local or by systemic administration of the active ingredient to the host.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dehydrate and other such material known to those of ordinary skill in the art.

The term "sweetening agent" as used herein is intended to mean a compound used to impart sweetness to a preparation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in tablet granulations. Such compounds include, by way of example and without limitation, acacia alginic acid, tragacanth, carboxymethylcellulose sodium, poly (vinylpyrrolidone), compressible sugar (e.g., NuTab), ethylcellulose, gelatin, liquid glucose, methylcellulose, povidone and pregelatinized starch, combinations thereof and other material known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC™ F68, PLURONIC™ F127), collagen, albumin, celluloses in nonaqueous solvents, combinations thereof and the like. Other binders include, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art.

The term "diluent" or "filler" as used herein is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in tablet and capsule formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein is intended to mean substances used in tablet formulations to reduce friction during tablet compression. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starched thereof, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN™s), polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethylcellulose, hydroxylpropylcellulose, hydroxypropylmethylcellulose phthalate, noncrystalline cellulose, magnesium aluminum silicate, triethanolamine, polyvinyl alcohol, polyvinylpyrrolidone (PVP), tyloxapol (a nonionic liquid polymer of the alkyl aryl polyether alcohol type, also known as superinone or triton), combinations thereof and other such materials known to those of ordinary skill in the art.

Most of these excipients are described in detail in, e.g., Howard C. Ansel et al., Pharmaceutical Dosage Forms and Drug Delivery Systems, (7th Ed. 1999); Alfonso R. Gennaro et al., Remington: The Science and Practice of Pharmacy, (20th Ed. 2000); and A. Kibbe, Handbook of Pharmaceutical Excipients, (3rd Ed. 2000), which are incorporated by reference herein.

DETAILED DESCRIPTION OF THE PREFERRED EMBODIMENTS

One embodiment of the present invention is directed to a novel polymorph form of lercanidipine hydrochloride, designated polymorph form V. The novel polymorph form V of lercanidipine hydrochloride may be characterized by, for example, X-ray powder diffraction pattern and/or melting point. The powder XRD spectrum for polymorph form V is presented in FIG. 1, and is set forth in tabular form in Table I below. The X-Ray powder diffraction was measured by an X-ray powder Diffractometer equipped with a Cu-anode (λ=1.54 Angstrom), X-ray source operated at 45 kV, 40 mA and a Ni filter is used to strip K-beta radiation. Two-theta calibration is performed using an NIST SRM 640c Si standard. The sample was analyzed using the following instrument parameters: measuring range=2-50° 2θ; step width=0.017°; and measuring time per step=5 sec.

TABLE 1

| 2θ | Relative Intensity (%) |
| --- | --- |
| 7.5567 | 24.60 |
| 10.8095 | 25.08 |
| 11.5702 | 44.58 |
| 11.7830 | 33.49 |
| 12.9422 | 12.58 |
| 13.4256 | 23.29 |
| 14.5405 | 12.60 |
| 15.1595 | 100.00 |
| 15.8627 | 20.42 |
| 16.5901 | 28.77 |
| 16.9949 | 26.39 |
| 17.2752 | 49.84 |
| 17.9432 | 35.18 |
| 19.4545 | 20.72 |
| 19.8836 | 55.07 |
| 20.7967 | 50.73 |
| 21.4870 | 43.92 |
| 22.5097 | 29.56 |
| 23.9261 | 8.41 |
| 24.6309 | 43.50 |
| 25.6598 | 27.78 |
| 27.4245 | 11.03 |
| 29.0007 | 16.64 |
| 30.1320 | 15.10 |
| 30.7263 | 8.19 |
| 33.4079 | 5.76 |
| 36.0060 | 8.13 |
| 38.9590 | 6.69 |
| 39.8607 | 6.22 |
| 41.6170 | 6.11 |

As shown in FIG. 2, polymorph form V of lercanidipine hydrochloride exhibits a predominant endotherm peak at about 179.5° C. as measured by a Differential Scanning Calorimeter (DSC 822, Mettler Toledo) at a scan rate of 10° C. per minute with an Indium standard. In this regard, it should be understood that the endotherm measured by a particular differential scanning calorimeter is dependent upon a number of factors, including the rate of heating (i.e., scan rate), the calibration standard utilized, instrument calibration, relative humidity, and upon the chemical purity of the sample being tested. Thus, an endotherm as measured by DSC on the instrument identified above may vary by as much as ±1° C. or even ±1 1/2° C. Accordingly, the term "about 179.5° C." is intended to encompass such instrument variations.

In one embodiment, polymorph form V of lercanidipine hydrochloride may be prepared by at least:

(a) dissolving lercanidipine hydrochloride in an alcohol-containing solvent to obtain a solution;

(b) adding an aliphatic ester-containing solvent to the solution of step (a); and (c) recovering lercanidipine hydrochloride substantially in polymorph form V from the solution.

In step (a) of the process of the present invention, lercanidipine hydrochloride is dissolved in an alcohol-containing solvent. The lercanidipine hydrochloride may be prepared using methods well known in the art or from commercial sources and do not constitute a part of the present invention.

Suitable alcohol-containing solvents include aromatic and aliphatic $C_1$-$C_{12}$ alcohols and the like and mixtures thereof. Suitable aliphatic alcohols include $C_1$-$C_8$ alcohols such as, for example, methanol, ethanol, n-propanol, isopropanol, n-butanol, isobutanol, tert-butanol and the like and mixtures thereof. Suitable aromatic alcohols include $C_3$-$C_{12}$ alcohols such as, for example, benzyl alcohol, benzyloxyethanol, phenoxyethanol and the like and mixtures thereof. Generally, the alcohol-containing solvent can be present in a ratio of about 1:1 v/w with respect to the lercanidipine hydrochloride. The lercanidipine hydrochloride and alcohol-containing solvent (s) may be heated to a temperature ranging from about 40° C. to about 60° C., preferably from about 45° C. to about 55° C., and most preferably from about 50° C. to about 55° C. for a time period ranging from about 30 minutes to about 40 minutes. The solution is preferably cooled to room temperature, a temperature ranging from about 25° C. to about 30° C.

In step (b) of the process of the present invention, an aliphatic ester-containing solvent is added to the solution. Suitable aliphatic ester-containing solvents include ester groups having from about 2 to about 12 carbon atoms, e.g., ethyl acetate, isopropyl acetate and the like and mixtures thereof. The aliphatic ester-containing solvent may be present in a ratio of about 10:1 v/w with respect to the lercanidipine hydrochloride. The aliphatic ester-containing solvent is preferably added at room temperature, a temperature in the range of from about 25° C. to about 30° C.

In step (c) of the process of the present invention, lercanidipine hydrochloride substantially in polymorph form V is recovered from the solution. Polymorph form V of lercanidipine hydrochloride can be recovered by, for example, crystallizing the solution of step (b) to produce substantially pure lercanidipine hydrochloride crystals; and isolating the crystals by techniques known in the art, e.g., filtration, to obtain polymorph form V of lercanidipine hydrochloride. The isolated crystals can then be further dried. Crystallization can be carried out by stirring the solution at about 60 to about 100 revolutions per minute (rpm) for a time period ranging from about 1 hour to about 16 hours. The temperature during stirring can range from about 25° C. to about 30° C. The resulting solid can then be filtered and washed with an ester-containing solvent, e.g., isopropyl acetate, (about 1:1 v/w, solvent:lercanidipine hydrochloride) to provide crystals of lercanidipine hydrochloride. The crystals may then be dried. The crystals may be dried at a temperature ranging from about 50° C. to about 55° C. until a loss on drying ("LOD") of less than about 10% is achieved. The time period for drying can range from about 6 hours to about 12 hours, and preferably about 8 hours.

Certain operational steps are well known in the art and, unless otherwise indicated, any known method for performing these functions may be used in the processes of this invention. For example, solvents may be removed by distillation in atmosphere or under vacuum. Drying may be accomplished by evaporation, spray drying, drying under vacuum, and freeze-drying. Stirring means any method for blending or mixing a reaction mixture.

In another embodiment, highly purified lercanidipine hydrochloride can be obtained by (a) reacting a solution comprising butanoic acid, 2-[(3-nitrophenyl)methylene]-3-oxo-2-[(3,3-diphenyl propyl)methylamino]-1,1-dimethyl ethyl ester hydrochloride and methylene dichloride, with methyl 3-amino crotonate and n-propanol and adjusting the pH of the solution to about 8 to about 9 with a base;

(b) cooling the reaction mass to a temperature of about 50° C. to about 55° C., distilling out n-propanol to obtain a residue, dissolving the residue in n-propanol, adjusting the pH of the reaction mass using n-propanol/HCl and distilling off n-propanol to obtain a residue;

(c) dissolving the residue in isopropyl acetate, washing with water, charcoalizing the solution and distilling off the isopropyl acetate to obtain a residue;

(d) dissolving the residue in methanol and isopropyl acetate, seeding the solution with polymorph form V of lercanidipine hydrochloride, and filtering and washing the solids; and (e) drying the solids obtained in step (d) to obtain substantially pure lercanidipine hydrochloride.

In step (a) of the process of the present invention, butanoic acid, 2-[(3-nitrophenyl)methylene]-3-oxo-2-[(3,3-diphenyl propyl)methylamino]-1,1-dimethyl ethyl ester hydrochloride solution (about 77% w/v) in a halogenated hydrocarbon solvent, e.g., methylene dichloride, is reacted with methyl 3-amino crotonate and n-propanol. The hydrochloride solution is reacted with the methyl 3-amino crotonate in about a 1:1 molar ratio. The reaction may take place at a temperature ranging from about 70° C. to about 90° C., and preferably from about 75° C. to about 80° C. The time period for the reaction can range from about 8 hours to about 12 hours, and preferably for about 10 hours. After the reaction, the pH of the reaction mass can be adjusted to about 8 to about 9 using a suitable base, e.g., a trialkylamine such as triethylamine.

In step (b) of the process of the present invention, the reaction mass is cooled to a suitable temperature and then n-propanol is removed, e.g., by distillation. A suitable temperature will ordinarily range from about 40° C. to about 70° C. and preferably from about 50° C. to about 55° C. The residue thus obtained can then be re-dissolved in n-propanol. This dissolution may take place at room temperature, a temperature ranging from about 25° C. to about 30° C. The pH of the reaction mass can then be adjusted to about 3 to about 4 using a n-propanol/HCl (20%) solution and the n-propanol is distilled off. This distillation may take place at a temperature below about 35° C.

In step (c) of the process of the present invention, the residue is dissolved in isopropyl acetate and washed with water. The solution is then charcoalized with a suitable charcoalizing agent such as activated charcoal. The isopropyl acetate is then distilled off. This distillation may take place at a temperature below about 35° C. and can range from about 25 to about 35° C.

In step (d) of the process of the present invention, the residue is dissolved in a solution of methanol and isopropyl acetate. This dissolution may take place at room temperature. If desired, the solution can be seeded with polymorph form V of lercanidipine hydrochloride. Polymorph form V of lercanidipine hydrochloride can be obtained by the process discussed hereinabove. During seeding, the solution may be stirred at about 15 to about 18 rotations per minute (rpm). The crystallization may take place at room temperature for about 20 hours to about 28 hours, and preferably for about 24 hours. The solids are then filtered and optionally washed with isopropyl acetate.

In step (e) of the process of the present invention, the solids are dried to obtain substantially pure lercanidipine hydrochloride. The solids may be dried at a temperature ranging from about 50° C. to about 55° C.

Another embodiment of the present invention provides a process for purifying lercanidipine hydrochloride. It has been found that the use of an alcohol-containing solvent, e.g., methanol, and an ester-containing solvent, e.g., isopropyl acetate, can be very effective in substantially eliminating the impurities found in lercanidipine hydrochloride, particularly the 1,4-dihydro-2,6-dimethyl-4-(3-nitrophenyl)pyridine-3,5-dicarboxylic acid 2-[N-(3,3-diphenyl propyl)-N-methylamino]-1,1-dimethyl ethyl propyl diester impurity discussed hereinabove. The process includes at least dissolving crude lercanidipine hydrochloride in an alcohol-containing solvent such as methanol, adding an aliphatic ester-containing solvent such as isopropyl acetate and then recovering substantially pure lercanidipine hydrochloride by, for example, crystallization, as discussed hereinabove.

In still another embodiment of the present invention, a purification process of lercanidipine hydrochloride includes at least the steps of (a) a first dissolution, (b) a second dissolution, (c) crystallization, and (d) drying. In step (a) of the purification process of this embodiment of the present invention, lercanidipine hydrochloride is substantially dissolved in an alcohol-containing solvent such as a $C_1$-$C_8$ alcohol, e.g., methanol, ethanol, isopropanol, butanol and the like and mixtures thereof. Generally, the alcohol-containing solvent is present in a ratio of about 1:1 v/w with respect to the lercanidipine hydrochloride. The lercanidipine hydrochloride and alcohol-containing solvent may be heated to a temperature ranging from about 40° C. to about 65° C. for a time period ranging from about 20 minutes to about 1 hour. The solution can then be cooled to room temperature, a temperature ranging from about 25° C. to about 30° C.

In step (b) of the purification process of this embodiment of the present invention, the dilution further includes adding to the solution an aliphatic ester-containing solvent such as an ester group having from about 2 to about 12 carbon atoms, e.g., isopropyl acetate. The aliphatic ester-containing solvent may be present in a ratio of about 10:1 v/w with respect to the lercanidipine hydrochloride. The aliphatic ester can be added at room temperature, a temperature in the range of from about 25° C. to about 30° C.

In step (c) of the purification process of this embodiment of the present invention, the solution may be stirred at a temperature ranging from about 25° C. to about 30° C. The solution may be stirred at about 60 rpm to about 100 rpm for a time period ranging from about 12 hours to about 20 hours. The resulting solid can then be isolated by conventional techniques, e.g., filtration, and optionally washed with a suitable solvent such as isopropyl acetate (about 1:1 v/w, isopropyl acetate:lercanidipine hydrochloride), to provide crystals of lercanidipine hydrochloride.

In step (d) of the purification process of this embodiment of the present invention, the crystals may be dried at a temperature ranging from about 50° C. to about 55° C. until the LOD is less than about 10%, over a time period of about 6 to about 12 hours, and preferably in about 8 hours.

By performing the purification processes of the present invention, substantially pure lercanidipine hydrochloride can be prepared with a degree of purity greater than or equal to about 98.5%, preferably greater than or equal to about 99.5% and more preferably greater than or equal to about 99.7%. The purity of the lercanidipine hydrochloride of the present invention may be determined by any method known in the art, e.g., high performance liquid chromatography (HPLC) analysis.

Another embodiment of the present invention provides a process for the preparation of an amorphous form of lercanidipine hydrochloride. It has been found that purified lercanidipine hydrochloride in a suitable organic solvent such as an alcohol-containing solvent, e.g., methanol, that is combined with a clarifying agent such as activated charcoal and then mixed with water is advantageously effective in the preparation of amorphous lercanidipine hydrochloride with substantially no change in the impurity profile. Generally, the process includes at least (a) dissolving purified lercanidipine hydrochloride as obtained hereinabove in an organic solvent, (b) treating the solution with a clarifying agent to form a clarified solution, and (c) recovering the amorphous form of lercanidipine hydrochloride. In one embodiment, the purified lercanidipine hydrochloride for use in forming the amorphous purified lercanidipine hydrochloride of the present invention is lercanidipine hydrochloride substantially in polymorph form V as discussed hereinabove.

In another embodiment of the present aspect, a process for the preparation of amorphous lercanidipine hydrochloride includes the steps of (a) dissolution, (b) treatment with a clarifying agent, (c) concentration, (d) redissolution, (e) addition, and (f) recovery.

In step (a) of the process of the present invention, substantially pure lercanidipine hydrochloride or lercanidipine hydrochloride substantially in polymorph form V is dissolved in an organic solvent such as an alcohol-containing solvent as discussed above. The organic solvent may be present in the ratio of about 10:1 v/w with respect to the lercanidipine hydrochloride. The clear solution of lercanidipine hydrochloride and organic solvent may be prepared at room temperature, a temperature ranging from about 25° C. to about 30° C.

In step (b) of the process of the present invention, a suitable clarifying agent can be added to the clear solution. Any of the many such agents that are known to be useful for adsorbing impurities in synthetic purification regimes can be employed. In one preferred embodiment, the clarifying agent is activated charcoal. The clarifying agent may be present in the ratio of about 0.05:1 w/w with respect to the lercanidipine hydrochloride. The solution may be stirred at a temperature ranging from about 25° C. to about 30° C. for a time period ranging from about 2 minutes to about 10 minutes, and preferably from about 3 minutes to about 5 minutes. The solution can then be filtered, e.g., through a hyflow bed, at a temperature ranging from about 25° C. to about 30° C. The hyflow bed can be washed with an alcohol (e.g., about 2:1 v/w with respect to the lercanidipine hydrochloride).

In step (c) of the process of the present invention, concentration may be carried out by any convenient means used to concentrate a solution, for example distillation at atmospheric pressure. In one embodiment, concentration may be carried out by distilling of the clear filtered solution at a temperature ranging from about 25° C. to about 30° C. under vacuum (not less than about 700 mm) until substantially no distillate is observed.

In step (d) of the process of the present invention, redissolution includes dissolving the residue obtained after concentration in the same or different organic solvent such as an alcohol-containing solvent as discussed above. The organic solvent may be present in a ratio of about 1:1 v/w with respect to the lercanidipine hydrochloride. The clear solution of lercanidipine hydrochloride and alcohol-containing solvent may be prepared at room temperature, a temperature ranging from about 25° C. to about 30° C.

In step (e) of the process of the present invention, water is added to the clear solution. The water may be present in the ratio of about 50:1 v/w with respect to the purified lercanidipine hydrochloride. The addition may be done for a time period ranging from about 45 minutes to about 60 minutes. The addition of the clear solution of lercanidipine hydrochloride and alcohol-containing solvent to water may be stirred at a temperature in the range of from about 30° C. to about 35° C. for a time period ordinarily ranging from about 25 to about 35 minutes after the addition of the clear solution to water.

In step (f) of the process of the present invention, the amorphous lercanidipine hydrochloride can be recovered by, for example, collecting the precipitate of the amorphous lercanidipine hydrochloride. This can be accomplished by techniques known in the art, e.g., filtration. Alternatively, the amorphous lercanidipine hydrochloride can be recovered by crystallization. Crystallization can be carried out by, for example, cooling the aqueous solution to a temperature ranging from about 0° C. to about 5° C. The reaction mixture may be further maintained at a temperature ranging from about 0° C. to about 5° C. for a time period ordinarily ranging from about 1 to about 4 hours, and preferably about 3 hours. The resulting solids may then be filtered and washed with water (e.g., about 2:1 v/w with respect to the lercanidipine hydrochloride). The resulting crystals can be dried, e.g., under vacuum (not less than about 700 mm) at a temperature ranging from about 60° C. to about 65° C. until the moisture content is less than about 2%, over a time period of about 6 to about 12 hours, and preferably about 8 hours.

By performing this process of the present invention, substantially pure amorphous lercanidipine hydrochloride can be prepared with a degree of purity greater than about 95%, preferably greater than about 97% and most preferably greater than about 99.75%. The amorphous form of the product can be determined by Powder X-Ray Diffractometry as discussed hereinabove.

Another embodiment of the present invention provides lercanidipine hydrochloride substantially free of 1,4-dihydro-2,6-dimethyl-4-(3-nitrophenyl)pyridine-3,5-dicarboxylic acid 2-[N-(3,3-diphenyl propyl)-N-methylamino]-1,1-dimethyl ethyl propyl diester. The term "lercanidipine hydrochloride substantially free of 1,4-dihydro-2,6-dimethyl-4-(3-nitrophenyl)pyridine-3,5-dicarboxylic acid 2-[N-(3,3-diphenyl propyl)-N-methylamino]-1,1-dimethyl ethyl propyl diester" as used herein shall be understood to mean lercanidipine hydrochloride formed with little to no content of 1,4-dihydro-2,6-dimethyl-4-(3-nitrophenyl)pyridine-3,5-dicarboxylic acid 2-[N-(3,3-diphenyl propyl)-N-methylamino]-1,1-dimethyl ethyl propyl diester. In this manner, the amount of 1,4-dihydro-2,6-dimethyl-4-(3-nitrophenyl)pyridine-3,5-dicarboxylic acid 2-[N-(3,3-diphenyl propyl)-N-methylamino]-1,1-dimethyl ethyl propyl diester, if present, resulting from the process for preparing lercanidipine hydrochloride present will be in relatively minor amounts, e.g., less than about 0.15 weight percent, preferably less than about 0.1 weight percent and most preferably 0 weight percent with respect to lercanidipine hydrochloride.

Yet another embodiment of the present invention is directed to pharmaceutical compositions containing at least a therapeutically effective amount of the lercanidipine hydrochloride of the present invention. Such pharmaceutical compositions may be administered to a mammalian patient in any dosage form, e.g., liquid, powder, elixir, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, troches, sachets, suspensions, powders, lozenges, elixirs and the like. The lercanidipine hydrochloride of the present invention may also be administered as suppositories, ophthalmic ointments and suspensions, and parenteral suspensions, which are administered by other routes. The dosage forms may contain the lercanidipine hydrochloride of the present invention as is or, alternatively, may contain the lercanidipine hydrochloride of the present invention as part of a composition. The pharmaceutical compositions may further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described hereinabove.

Capsule dosages will contain the lercanidipine hydrochloride of the present invention within a capsule which may be coated with gelatin. Tablets and powders may also be coated with an enteric coating. The enteric-coated powder forms may have coatings containing at least phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, they may be employed with suitable plasticizers and/or extending agents. A coated capsule or tablet may have a coating on the surface thereof or may be a capsule or tablet comprising a powder or granules with an enteric-coating.

Tableting compositions may have few or many components depending upon the tableting method used, the release rate desired and other factors. For example, the compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols like mannitol and sorbitol, acrylate polymers and copolymers, as well as pectin, dextrin and gelatin.

Other excipients contemplated by the present invention include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

In one embodiment, the lercanidipine hydrochloride disclosed herein for use in the pharmaceutical compositions of the present invention can have a $D_{50}$ and $D_{90}$ particle size of less than about 400 microns, preferably less than about 200 microns, more preferably less than about 150 microns, still more preferably less than about 50 microns and most preferably less than about 15 microns. It is noted the notation $D_x$ means that X % of the particles have a diameter less than a specified diameter D. Thus, a $D_{50}$ of about 400 microns means that 50% of the micronized particles in a composition have a diameter less than about 400 microns. The term "micronization" used herein means any process or methods by which the size of the particles is reduced. For example, the particle sizes of the lercanidipine hydrochloride of the present invention can be obtained by any milling, grinding, micronizing or other particle size reduction method known in the art to bring the solid state form of the lercanidipine hydrochloride of the present invention into any of the foregoing desired particle size range. As also used herein, lercanidipine hydrochloride particles with reduced size are referred to as "micronized particles of lercanidipine hydrochloride" or "micronized lercanidipine hydrochloride".

Actual dosage levels of the lercanidipine hydrochloride of the present invention may be varied to obtain an amount of the lercanidipine hydrochloride of the present invention that is effective to obtain a desired therapeutic response for a particular composition and method of administration. The selected dosage level therefore depends upon such factors as, for example, the desired therapeutic effect, the route of administration, the desired duration of treatment, and other factors. The total daily dose of the compounds of this invention administered to a host in single or divided dose and can vary widely depending upon a variety of factors including, for example, the body weight, general health, sex, diet, time and route of administration, rates of absorption and excretion, combination with other drugs, the severity of the particular condition being treated, etc. The pharmaceutical compositions herein can formulated in any release form, e.g., immediate release, sustained release, controlled release, etc.

The following examples are provided to enable one skilled in the art to practice the invention and are merely illustrative of the invention. The examples should not be read as limiting the scope of the invention as defined in the features and advantages.

EXPERIMENTAL

The purity was measured by HPLC under the following conditions:
Column: $C_8$ Waters symmetry, 250×4.6 mm, 5µ
Column temperature: 25° C.
Moving phase: Buffer:Acetonitrile (48:52, v/v)
Buffer: 0.15 M of sodium perchlorate in water. Adjust pH to 4.0 with 1% perchloric acid
Detector: UV, 220 nm
Flow rate: 1.5 ml/min.
Injection Volume: 20 µl
Run Time: 60 minutes
Retention time: 15.5 minutes

Example 1

Preparation of Lercanidipine Hydrochloride

Into a 2 L 4-neck round bottom flask, butanoic acid, 2-[(3-nitrophenyl)methylene]-3-oxo-2-[(3,3-diphenyl propyl)methylamino]-1,1-dimethyl ethyl ester hydrochloride (30 g) in methylene dichloride (39 ml) and n-propanol (300 ml), were charged at a temperature ranging from about 25° C. to about 30° C. Triethylamine (15 g) was added to adjust the pH to about 8 to about 9, as tested on pH paper. Methyl 3-amino crotonate (6.28 g) was added. The reaction mixture was heated to a temperature ranging from about 75° C. to about 80° C. and stirred for about 10 hours. The reaction mixture was cooled and n-propanol was distilled out under vacuum completely at a temperature ranging from about 50° C. to about 55° C. The residue was dissolved in n-propanol (150 ml) at a temperature ranging from about 30° C. to about 35° C. and then cooled to a temperature ranging from about 25° C. to about 30° C. N-propanol/HCl (10 ml, 20% HCl) was slowly added while maintaining the reaction mass at room temperature to adjust the pH to about 3 to about 4, as tested on pH paper. The reaction mixture was maintained for about 30 minutes at room temperature. N-propanol was stripped out with isopropyl acetate (60 ml) at a temperature ranging from about 30° C. to about 35° C. The residue was dissolved in isopropyl acetate (180 ml) and washed with water (2×180 ml).

Activated charcoal (3 g) was added to the organic layer and stirred for about 15 minutes at a temperature ranging from about 25° C. to about 30° C. The organic layer was filtered through a hyflo bed and washed with isopropyl acetate (30 ml). The isopropyl acetate was distilled out completely under vacuum at a temperature below about 35° C. and degassed for about 2 hours at a temperature below about 35° C. The residue was dissolved in methanol (15 ml) and isopropyl acetate (300 ml) at room temperature. The solution was seeded with pure lercanidipine hydrochloride in polymorph form V (30 g) and stirred with at about 15 rpm to about 18 rpm for about 24 hours. The solids were filtered and washed with isopropyl acetate (30 ml). The wet cake weighed about 25 grams. The product was dried in an oven at a temperature ranging from about 50° C. to about 55° C. for about 8 hours wherein the loss on drying (LOD) was less than about 10.0%. The dried product was lercanidipine hydrochloride weighing about 15 grams, with a yield of about 42% and purity of about 98.5% as determined by HPLC.

Example 2

Preparation of Polymorph Form V of Lercanidipine Hydrochloride

Into a 2 L 4-necked round bottom flask, lercanidipine hydrochloride (110 g; purity of about 98.5%) of Example 1 and methanol (110 ml) were added at room temperature, a temperature ranging from about 25° C. to about 30° C., under stirring. The reaction mixture was then heated to a temperature ranging from about 50° C. to about 55° C. and maintained for about 30 minutes. The reaction mixture was then cooled to room temperature. Isopropyl acetate (1100 ml) was added to the cooled solution at room temperature and maintained for about 16 hours at room temperature with a stirrer speed of about 60 rpm to about 100 rpm. The precipitated solid was filtered and washed with isopropyl acetate (110 ml). The wet cake weighed about 132 g.

The product was dried in an oven at a temperature ranging from about 50° C. to about 55° C. for about 8 hours wherein the LOD was less than about 10.0%. The dried product weighed about 86.9 grams, with a yield of about 79% and purity greater than about 99.7% as determined by HPLC. All the individual impurities were below about 0.07 wt. %.

The XRD and DSC of the final product are set forth in FIGS. 1 and 2 and were recorded and identified as polymorph form V of lercanidipine hydrochloride.

Example 3

Purification of Polymorph Form V of Lercanidipine Hydrochloride

Into a 2 L 4-necked round bottom flask, lercanidipine hydrochloride (110 g; purity of about 98.5%) of Example 1 and methanol (110 ml) were added at a temperature ranging from about 25° C. to about 30° C. under stirring. The reaction mixture was then heated to a temperature ranging from about 50° C. to about 55° C. and maintained for about 30 minutes. Cold water was circulated to the condenser. Next, the clear reaction mass was brought to room temperature. This was followed by addition of isopropyl acetate (1100 ml) at room temperature and maintained for about 16 hours at about 60 to about 100 rpm. The precipitated solid was filtered and washed with isopropyl acetate (110 ml). The wet cake weighed about 132.0 g.

The product was dried in an oven at a temperature in the range of from about 50° C. to about 55° C. for about 8 hours wherein the LOD was less than about 10.0%. The dried product was polymorph form V of lercanidipine hydrochloride weighing about 86.9 g, with a yield of about 79% and purity greater than about 99.7% as determined by HPLC. All the individual impurities are below about 0.07 wt. %.

Example 4

Preparation of Amorphous Lercanidipine Hydrochloride

In a clean and dry 2 L 4-necked round bottomed flask, purified lercanidipine hydrochloride (100.0 g, purity of about 99.7%) obtained in Example 3 and methanol (1.0 L) were charged at room temperature. The reaction mass was stirred at room temperature until a clear solution was obtained. Activated charcoal (5.0 g) was added and stirred for about 5 minutes at room temperature. The reaction mixture was filtered through a hyflow bed and washed with methanol (200.0 ml). The clear filtrate was collected in a cleaned and dried 2 L round bottomed flask. The methanol was distilled under vacuum (not less than 700 mm) completely at room temperature. The residue was re-dissolved in methanol (100.0 ml) at room temperature.

In a clean 10 L 4-necked round bottomed flask, demineralized (DM) water (5.0 L) was charged. The methanol solution containing the residue was added to the DM water slowly with stirring over a period of about 45 minutes to about 60 minutes at a temperature ranging from about 30° C. to about 35° C. The reaction mass was stirred for about 30 minutes at a temperature ranging from about 30° C. to about 35° C. The reaction mass was cooled to a temperature ranging from about 0° C. to about 5° C. The reaction mass was stirred at a temperature ranging from about 0° C. to about 5° C. for about 3 hours. The solids were filtered off and washed with DM water (200.0 ml). The wet cake weighed about 175.0 g.

Figure 3:
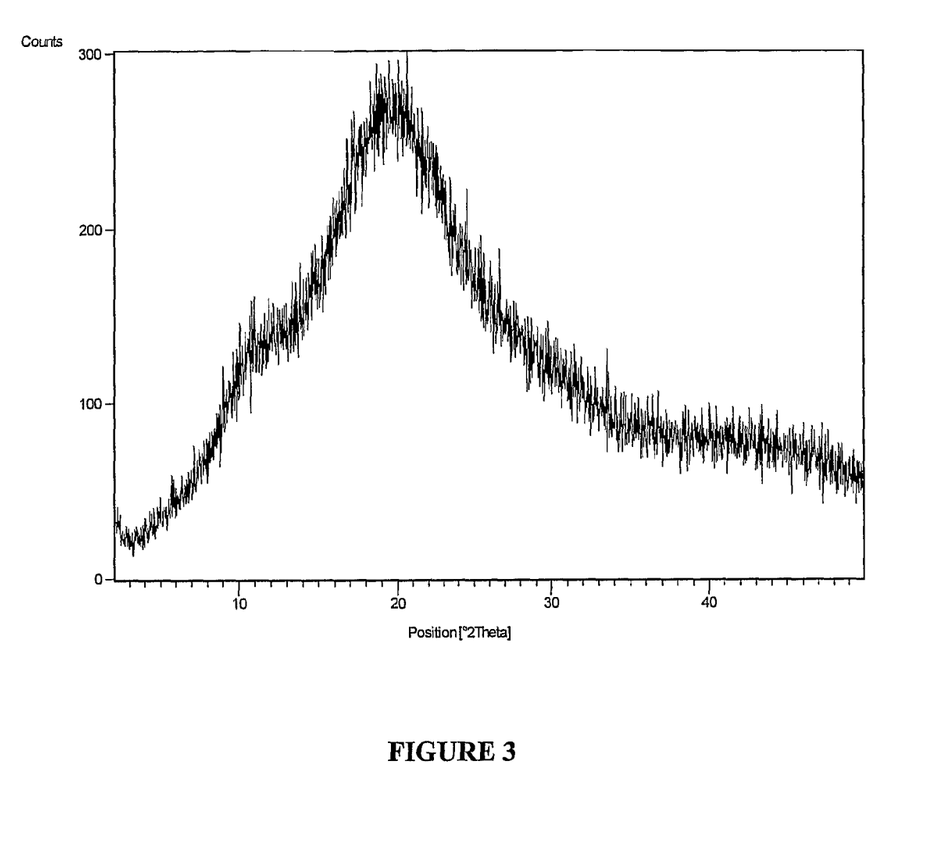
FIG. 3 is a characteristic X-ray powder diffraction pattern of lercanidipine hydrochloride in an amorphous form.

Next, the product was dried in a vacuum oven (vacuum not less than 700 mm) at a temperature ranging from about 60° C. to about 65° C. for about 8 hours wherein the moisture content was below 2%. FIG. 3 is a characteristic X-ray powder diffraction pattern showing that the dried product was the purified amorphous lercanidipine hydrochloride. The purified amorphous lercanidipine hydrochloride weighed about 70.0 grams, with a yield of about 70% and purity of about 99.7% as determined by HPLC.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. Lercanidipine hydrochloride substantially in polymorph form V, exhibiting characteristic peaks (expressed in degrees $2\theta \pm 0.2°\theta$) at about 15.1595, about 17.2752, about 19.8836, about 20.7967, and about 21.4870.

2. The lercanidipine hydrochloride substantially in polymorph form V of claim 1, exhibiting characteristic peaks (expressed in degrees 2θ±0.2°θ) at about 7.5567, about 10.8095, about 12.9422, and about 22.5097; and exhibiting a predominant endotherm peak at about 179.5° C.

3. The lercanidipine hydrochloride substantially in polymorph form V of claim 1, further characterized by exhibiting characteristic peaks (expressed in degrees 2θ±0.2°θ) at about 11.5702 and about 24.6309.

4. The lercanidipine hydrochloride substantially in polymorph form V of claim 1, having a purity of equal to or greater than about 98.5%.

5. A pharmaceutical composition comprising a therapeutically effective amount of the lercanidipine hydrochloride substantially in polymorph form V of claim 1.

6. The pharmaceutical composition of claim 5, wherein the lercanidipine hydrochloride substantially in polymorph form V is a micronized lercanidipine hydrochloride substantially in polymorph form V having a particle size of less than about 400 microns.

7. A process for the preparation of lercanidipine hydrochloride substantially in polymorph form V, the process comprising:
(a) dissolving lercanidipine hydrochloride in a $C_1$-$C_{12}$ aliphatic alcohol solvent to obtain a solution;
(b) adding a $C_2$-$C_{12}$ aliphatic ester solvent to the solution; and
(c) recovering lercanidipine hydrochloride substantially in polymorph form V.

8. The process of claim 7, wherein the recovering step comprises crystallizing the solution to produce lercanidipine hydrochloride crystals; and drying the lercanidipine hydrochloride crystals to obtain lercanidipine hydrochloride substantially in polymorph form V.

9. The process according of claim 8, wherein the lercanidipine hydrochloride substantially in polymorph form V is thereafter converted to lercanidipine hydrochloride in an amorphous form.

10. Lercanidipine hydrochloride substantially in polymorph form V, prepared by the process of claim 7.

11. A process for the preparation of substantially pure lercanidipine hydrochloride substantially in form V, the process comprising:
(a) reacting a solution comprising butanoic acid, 2-[(3-nitrophenyl)methylene]-3-oxo-2-[(3,3-diphenyl propyl)methylamino]-1,1-dimethyl ethyl ester hydrochloride and methylene dichloride, with methyl 3-amino crotonate and n-propanol and adjusting the pH of the solution to about 8 to about 9 with a base;
(b) distilling out n-propanol to obtain a residue;
(c) dissolving the residue in isopropyl acetate;
(d) treating the solution containing isopropyl acetate with a clarifying agent to form a clarified solution;
(e) concentrating the clarified solution to form a concentrated clarified solution; (f) dissolving the concentrated clarified solution in methanol and isopropyl acetate; (g) seeding the solution with a lercanidipine hydrochloride substantially in polymorph form V, and
(h) recovering the lercanidipine hydrochloride substantially in polymorph form V.

12. The process of claim 11, further comprising:
cooling the reaction mass to a temperature of about 50° C. to about 55° C.;
distilling out n-propanol to obtain a first residue;
dissolving the first residue in n-propanol,
adjusting the pH of the reaction mass using n-propanol/HCl and distilling off n-propanol to obtain a second residue;
dissolving the second residue in isopropyl acetate and washing with water to obtain a solution;
charcoalizing the solution and distilling off the isopropyl acetate to obtain a third residue;
dissolving the third residue in methanol and isopropyl acetate,
seeding the solution with lercanidipine hydrochloride polymorph form V and filtering the solids; and
drying the solids to obtain lercanidipine hydrochloride substantially in polymorph form V.

13. Lercanidipine hydrochloride substantially in polymorph form V, substantially free of 1,4-dihydro-2,6-dimethyl-4-(3-nitrophenyl)pyridine-3,5-dicarboxylic acid 2-[N-(3,3-diphenyl propyl)-N-methylamino]-1,1-dimethyl ethyl propyl di-ester.

14. The pharmaceutical composition of claim 5, wherein the crystalline form of the lercanidipine hydrochloride is a micronized crystalline form of the lercanidipine hydrochloride having a particle size distribution equal to or less than about 200 microns.

15. The pharmaceutical composition of claim 5, wherein the crystalline form of the lercanidipine hydrochloride is a micronized crystalline form of the lercanidipine hydrochloride having a particle size distribution equal to or less than about 50 microns.

16. The pharmaceutical com 52position of claim 5, wherein the crystalline form of the lercanidipine hydrochloride is a micronized crystalline form of the lercanidipine hydrochloride having a particle size distribution equal to or less than about 15 microns.

* * * * *